United States Patent
St. Ores et al.

(10) Patent No.: US 7,594,889 B2
(45) Date of Patent: Sep. 29, 2009

(54) INTEGRATED DATA COLLECTION AND ANALYSIS FOR CLINICAL STUDY

(75) Inventors: John W. St. Ores, Stillwater, MN (US); Sarah A. Audet, Shoreview, MN (US); James K. Carney, Eden Prairie, MN (US); Janell M. Gottesman, St. Louis Park, MN (US); Adrianus P. Donders, Andover, MN (US); Michael R. Ujhelyi, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 340 days.

(21) Appl. No.: 11/097,685

(22) Filed: Mar. 31, 2005

(65) Prior Publication Data
US 2006/0224421 A1 Oct. 5, 2006

(51) Int. Cl.
*A61B 1/00* (2006.01)
(52) U.S. Cl. .......................... 600/301; 607/3
(58) Field of Classification Search ............. 600/300, 600/301, 513–528; 607/5
See application file for complete search history.

(56) References Cited

U.S. PATENT DOCUMENTS

| 6,879,970 | B2 | 4/2005 | Shiffman et al. | |
|---|---|---|---|---|
| 2002/0143563 | A1 | 10/2002 | Hufford et al. | |
| 2003/0036683 | A1* | 2/2003 | Kehr et al. | 600/300 |
| 2004/0059597 | A1* | 3/2004 | Tkaczyk et al. | 705/2 |
| 2004/0093240 | A1* | 5/2004 | Shah | 705/2 |
| 2004/0215258 | A1* | 10/2004 | Lovett et al. | 607/9 |
| 2006/0224326 | A1 | 10/2006 | St. Ores et al. | |
| 2006/0224421 | A1 | 10/2006 | St. Ores et al. | |

* cited by examiner

Primary Examiner—Scott M Getzow

(57) ABSTRACT

A data collection system includes remote, implantable sensors for monitoring one or more patient parameters, collecting and processing data from those sensors and utilizing that data in the performance of a clinical study of a drug or other pharmacological agent. The system assists with preparation of a protocol for a clinical trial; presentation of that protocol; assuring compliance with the protocol; and generating useful results from data collected via the system and externally for presentation to an approval forum.

20 Claims, 6 Drawing Sheets

INTEGRATED DATA COLLECTION AND ANALYSIS FOR CLINICAL STUDY

FIELD OF THE INVENTION

The present invention generally relates to conducting clinical evaluation of pharmacological products and more specifically to the collection and processing of data in furtherance of such a clinical evaluation.

DESCRIPTION OF THE RELATED ART

The Food and Drug Administration (FDA) is tasked with the responsibility of monitoring the safety and efficacy of new drugs or other controlled substances, pharmacological, biological, biomedical, pharmacological, or organically derived agents or compounds (collectively "drugs") used in the treatment, management, inhibition or prevention of a disease, symptom, condition, or other malady. The FDA must therefore balance the potential risk against the potential benefit in determining whether such a drug should receive governmental approval and if approved, determining (or approve) appropriate guidelines for that use.

The drug approval process is extremely time consuming, extremely expensive and has a relatively low rate of success. By some estimates it may take as long as 8-12 years to move a drug from the laboratory to the market, the approval process may cost upwards of $900 million dollars, and approximately one of every 5000 drugs submitted is eventually approved. Naturally, this limits the ability of any company and particularly smaller companies to introduce any product and tends to focus research away from more speculative drugs and therapies, which if pursued, may or may not yield successful products. Finally, this cost is born by the consumer in the form of tremendously high prescription drug costs and this subject continues to be one of the major social issues in current debate.

Of note, as drug research advances, more and more targeted drugs are being found. This allows the drug to be very effective for a very narrow focus or patient population. In other populations, this targeted drug may be toxic, harmful or unhelpful. Thus, similar populations may be underserved because the approved process is too impracticable for a company to identify, test and gain approval for these narrowly targeted drugs.

Another downside to the current methodology is the public perception of a lack of effectiveness in the FDA approval process. Various drugs are approved by the FDA and presumed safe in the public's eye and then, after a period of time, evidence establishes that the drugs are not safe or have unacceptable long-term consequences. In fairness, the approval process, by necessity, reviews "relatively" short-term effectiveness for specific conditions and any side effects that are apparent in that term. Requiring drugs to undergo additional years or decades of clinical evaluation will only worsen the problem. Furthermore, once a drug is approved end users will often use that drug for "off-label" purposes or in dosing that is beyond that approved by the FDA. Thus, while the drug may ultimately be safe and effective in the approved form and for the approved purposes, these off-label uses and negative consequences are imputed to the process. Of course, there is always a possibility that an approved drug will have negative consequences that are simply not known for many years and this necessitates the balancing of the risk versus the benefit.

Patients and doctors are not permitted to make this risk assessment for themselves during the FDA approval process. That is, a given drug may show promise and despite unknown risks, the severity of a given patient's condition may warrant, to the physician and/or patient, use of that drug. However, except in rare circumstances doctors are not permitted to prescribe that drug to that patient even with full awareness of the risks, full awareness of the uncertainty, and the consent of the patient. Thus, the approval process delays access to the drug and ultimately cannot guarantee safety or efficacy. Therefore, the balance between the safety margin provided by the FDA process and the ultimate uncertainty that will always remain is best managed by completing the FDA approval process as quickly, accurately and effectively as possible.

In order to understand the present invention, an understanding of an overview of the current FDA approval process is beneficial. Initially, a given company will create a drug that they suspect will be useful for treating some condition in humans. As indicated above, there is tremendous cost and tremendous risk of failure; thus, any given company will demand a high and demonstrable likelihood of success before rigorously pursuing the formal approval process.

This generally occurs in preclinical testing and is performed with in vitro testing, testing on tissue samples, cultures, computer modeling and animal testing. The purpose of these tests is to establish that the drug appears reasonably safe for human use and has an acceptable indication of treating a given condition.

Through animal testing and the like, effectiveness, toxicity, side effects, absorption rates, dosing rates (and their affect on the rest of the factors) is established or predicted. In practice, the researcher will provide varying levels of the drug to a variety of animals and monitor the results. Various physiologic sensory outputs can be gathered and recorded such as heart rate, neural activity, blood screening, and the like. Similarly, tissue samples may be taken as appropriate and the animal can be studied post mortem. Various conditions can be simulated or forced in the animal studies. For example, overdoses can be given, stress induced, injuries or diseases introduced, and environmental factors can be controlled/amplified and their effects and interaction with the drug determined. Furthermore, animals having other comorbidities can be included and the effect of the experimental drug on these conditions is also evaluated.

Assuming the drug is deemed effective or promising at this stage, a sponsor will file an Investigational New Drug (IND) application with the FDA. The sponsor (may also be the principle investigator) is a doctor, researcher or organization that is undertaking responsibility for conducting a clinical trial. While various entities may act as sponsors, the sponsor may contract with certain organizations to carry out or conduct aspects of the study and these organizations are designated as clinical research organizations (CRO). For purposes of the present invention, the terms CRO and sponsor are often used interchangeably as the functions and responsibilities often overlap, with the understanding that they are in fact different entities. The IND will include the results of the preclinical work and is a request to begin clinical study on humans. As such, the IND will include the protocol (complex in and of themselves) for the clinical trials, such as the number of patients, the dosages provides, the method of delivery, the chemical structure or composition of the drug and the qualifications of the clinicians, and the protocols for evaluating the patients. If approved by an Institutional Review Board (IRB), the sponsor may move forward with the clinical trials. The observations made during the preclinical study will help define specific concerns for the clinical trials. For example, perhaps a new drug has shown a modest elevation in blood pressure as a side effect in the animal studies. Blood pressure would be more carefully scrutinized in the human clinical trials as a result.

The clinical trials are typically performed within a medical institution e.g., hospital(s), clinic(s), university medial research center(s), etc. Often, the same drug will be tested under the same approved protocol at multiple sites, under the auspices of one sponsor. At each site, an on-site investigator is responsible for conducting the study at that site, is ultimately responsible for the administration of the drug to enrolled patients at that site, and is responsible for complying with the protocol. The drug is administered to patients under the immediate direction of the investigator. While a pharmaceutical company may submit an IND and conduct a trial, the sponsor is often separate and distinct from the pharmaceutical company. Thus, this avoids the perception of a conflict of interest or a perception of bias that may arise if the drug company solely conducted the study. The sponsor enrolls the statistically appropriate number of patients to provide a credible result. These patients are then individually seen and monitored by health care providers in compliance with the protocol and under the direction of the investigator at each site.

Clinical studies are typically conduced in three phases. In Phase I, the primary concern is patient safety (and not efficacy); thus, only a very small number of patient's are enrolled (typically less than 80-100). These patients are generally otherwise healthy and are only given small doses of the drug. Assuming safety is established, the process proceeds to Phase II.

Phase II typically includes double blind, randomized, highly controlled studies with the dual goal of further establishing safety but also showing efficacy. Often, this will include a control group not given the drug and/or other groups given other treatment regiments as well as the group given the new drug. Phase II studies usually include hundreds of patients.

Assuming an appropriate level of success, the Phase III trial may begin and may include many thousands of patients. As more patients are enrolled with more complex comorbidities and use the drug over an extended period of time, the effectiveness and any potential side effects are more likely to materialize.

At each point, the data is collected and provided to the FDA or the IRB and the FDA or the IRB determines whether the CRO may move from one phase to another. At the conclusion of Phase III, the sponsor or the company may submit an application to the FDA to market the drug based upon the results of the clinical studies. The FDA may approve the drug and the company can market it according to the parameters of the study. That is, safe dosages for the treatment of the specifically studied conditions can be promoted to health care providers or to the public for non-prescription drugs.

Subsequent to the approval of the drug, various entities conduct post market surveillance and continue to monitor the safety and efficacy of the drug. The drug company as well as health care providers and patients may report adverse effects that could result in the FDA withdrawing or modifying its approval.

As indicated, the protocols for conducting the study are very complex, rigorous and generally inflexible once generated. In addition, over the course of the study, information may come to light that necessitates a change to these protocols. As with any such study, human involvement and subjectivity introduce potential errors.

By way of example, consider a new drug intended to lower blood pressure called "BPX" that is about to enter a Phase III clinical study. A protocol had been submitted to and approved by the IRB. The protocol sets an end point or goal of the study. For example, the end point may be a reduction in blood pressure of at least 10% in 85% of the patients. Dosing is defined in the protocol. For example, a dose may constitute 5 mg for every 50 kg that the patient weighs. Scheduling is defined. Patients may be given an entire dose orally, once per day in morning; or given three times a day. Within the study, different dosages, timing, and method of administration may be applied to different patient populations to identify effectiveness.

Whatever these parameters are, they are provided to the physicians who are responsible for the enrolled patients (e.g., the investigator at a given site). The physicians will prescribe or administer the new drug BPX (or a placebo or another control drug) and periodically evaluate the patient's health and the effect of the drug on the patient. The frequency and extent of these patient evaluations is also defined by the protocol. For example, the protocol may indicate that the patient must be seen once per week for one year, and have their blood pressure, weight, and temperature measured, have their blood drawn and screened, have their kidney function evaluated, and take/update a medical history on every third visit.

As the trial progresses, any negative effects reported by the patient or determined by the physician are reported, regardless of their cause. For example, if the patient develops an infection that is most likely the result of an untreated cut, that information is collected and reported. Upon evaluation of the complete study data, this may prove to be irrelevant or might (when combined with other data) tend to indicate a reduced immune response in those patients taking BPX. In any event, all adverse affects are reported for subsequent evaluation.

In order for the study to have any real merit, there must be a sufficiently large sample of representative patients taking the drug. This will likely mean that there are a relatively large number of health care providers collecting information. Thus, this introduces a great opportunity for human error as well as for variance due to subjective interpretation of information. As an example, blood pressure measured with a sphygmomanometer requires a subjective determination of the termination and initiation of sounds resulting from fluid flow. Results from the same patient may vary depending upon the health care provider taking the measurement; furthermore, a single health care provider who routinely skews such a measurement may affect a large percent of the sample patient population if that health care provider is the one typically taking measurements for this study.

Patients may perceive symptoms quite differently and report them quite differently. Likewise, a given health care provider may be more or less aggressive with a given health history and may be more or less likely to pursue an indication of a symptom depending upon how the patient presents that symptom. The physician may be more or less likely to draw out information from patients, and a given patient may provide what they believe the physician "wants" to hear. In other words, this all becomes very subjective data collection.

In addition to errors introduced by health care providers, the patients themselves often introduce errors. One example is compliance. Patients may be expected to take the drug once per day, every day. Any given patient may forget to do so with varying degrees of frequency and may not be truthful about reporting their failure to comply. Conversely, a given drug may have either a real or perceived beneficial effect and the patients may increase their own dosage. Similarly, patients may tend to manipulate self-reported data. For example, the patient may be asked to weigh herself daily. The number may not be recorded truthfully out of vanity, fear that weight gain or loss will terminate the patient's participation in the study, or for any number of reasons.

Similarly, such data even when accurately recorded by a health care provider only represents a single point in time measurement. Thus, whether it is weight or blood pressure of some other parameter that value might not be truly representative of the patient over time. Blood pressure may be artificially increased by anxiety when seeing a doctor. Alternatively, the patient may routinely schedule the appointment at the same time each week. Perhaps the patient always fasts on that day or the day before; or alternatively, routinely dines at a favorite restaurant and has a very heavy meal just prior to the appointment. If reported, the health provider can account for these issues and perhaps reschedule if necessary; however, it is quite likely that these factors are often not reported. Such evaluation does not typically identify asymptomatic indicators or trends. For example, blood pressure may be rising by the patient does not perceive any symptoms. Therefore, if the singular measurements are below a threshold, the underlying data may be overlooked.

As the various healthcare providers collect information from their patients, the data is provided to one or more entities. These entities might include the FDA, the sponsor, the pharmaceutical company, an institutional review board, and/ or a data safety monitoring board. The data is evaluated on a periodic, on-going basis and if concerns are raised the protocol may be adjusted. Obviously, if a high number of deaths or serious illnesses/events occur that are likely related to the drug, the study may be temporarily or permanently terminated. Other variations may include a determination that the study protocol dosages are too high or too low; patients with particular comorbidities are at risk for complications and the like. The point of this ongoing evaluation is not to fully predict the study results but to ensure patient safety, ensure compliance with the protocol and to make any changes required to attempt to assure that the study will provide safe and useful results.

At some point, the sponsor collects all of the data, which usually includes a massive amount of information. The data may be provided to the FDA and to the pharmaceutical company. The various groups will then independently statistically analyze the data and the sponsor will present the conclusions to the FDA. Assuming favorable results indicating that BPX is safe and achieved the desired reduction in blood pressure, the FDA will approve the drug.

As illustrated, this process is replete with potential human factor errors. Yet, this serves as the process for determining whether new drugs should or should not be provided to the public. Of note, new medical devices undergo a similar approval process with the FDA, including clinical study.

DETAILED DESCRIPTION

Figure 1:
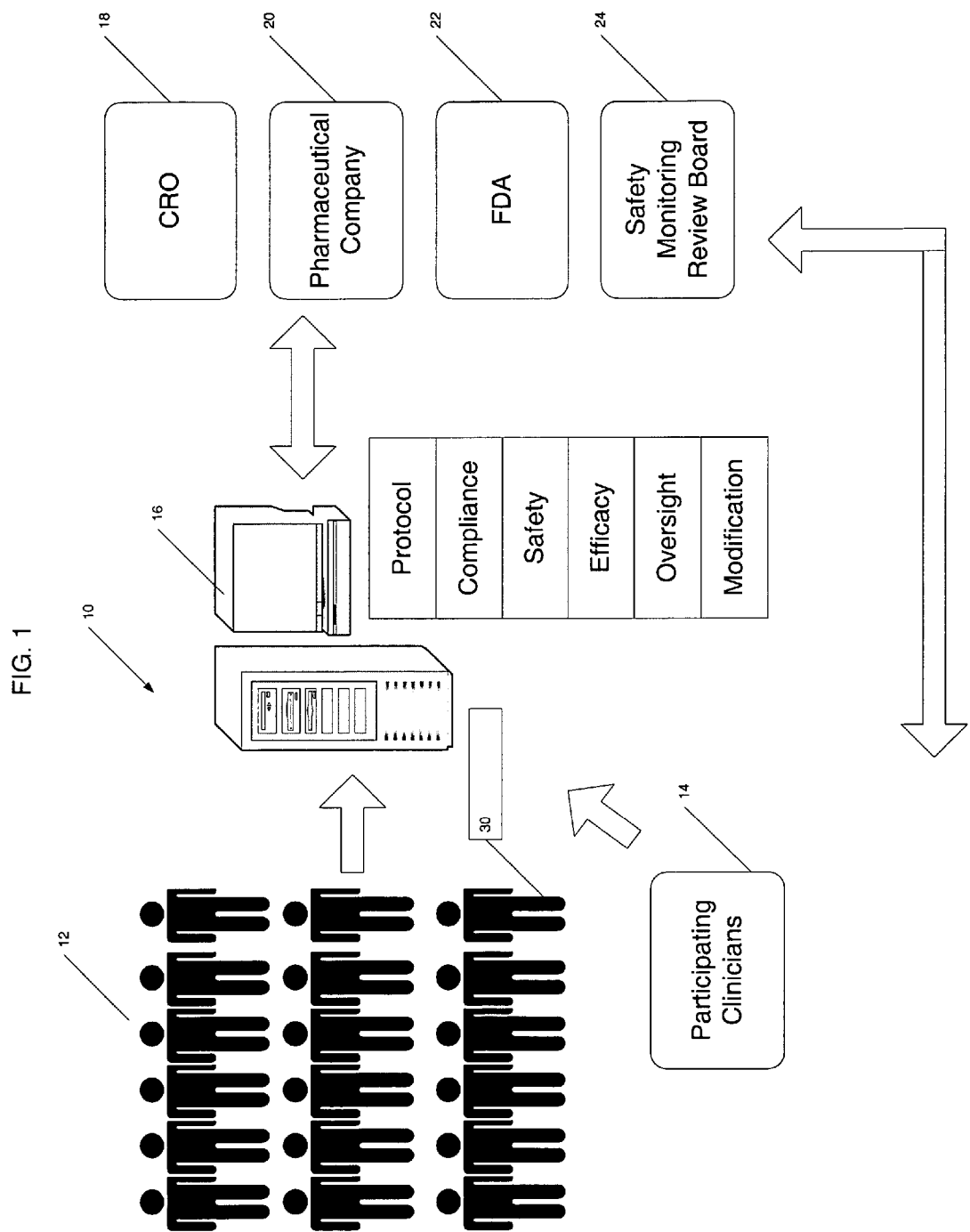
FIG. 1 is a schematic diagram illustrating a data collection system that interfaces with patients, clinicians, and end users of the data to conduct clinical evaluations.

The present invention provides a centralized data collection system that interfaces with patients, clinicians, and end users of the data to conduct clinical evaluations of, for example, new drugs for a regulatory approval process. FIG. 1 schematically illustrates this overall system 10. The patients participating in the study are collectively referred to as the patient population 12. Data is collected from the patient population 12 as well as participating clinicians and provided to a central server or host data collection system 16 that manages the clinical study. That is, the protocol of the study is generated on or provided to the central server 16 by the sponsor or clinical research organization (CRO) 18. In this manner, the central server 16 has oversight capability and, if designated, responsibility for providing the protocol to the participating clinicians 14 (investigators and those under their supervision), monitoring compliance, determining safety and efficacy on a real-time or near real-time basis as data is input, and permitting modification of the protocol at one location with dissemination to the participating clinicians.

The pharmaceutical company 20 responsible for creating the drug is also in communication with the central server 16. As information becomes available (and as permitted by the protocol or clinical study guidelines), that information is provided to the pharmaceutical company 20 so that they may monitor the progress of the evaluation. Likewise, new data that the pharmaceutical company generates may be provided to the central server 16. In the same manner, information is provided to the FDA 22, safety monitoring review board 24, and any other entity that needs access to the data and/or analysis provided on the central server 16 as appropriate.

In general, any of these entities may communicate with one another directly or via the central server 16. For example, the safety monitoring review board 24, investigational review board (IRB) or the FDA 22 may determine that an investigational drug is unsafe during the course of the study and may notify the clinicians 14 or patients 12 to discontinue use of the drug.

Figure 2:
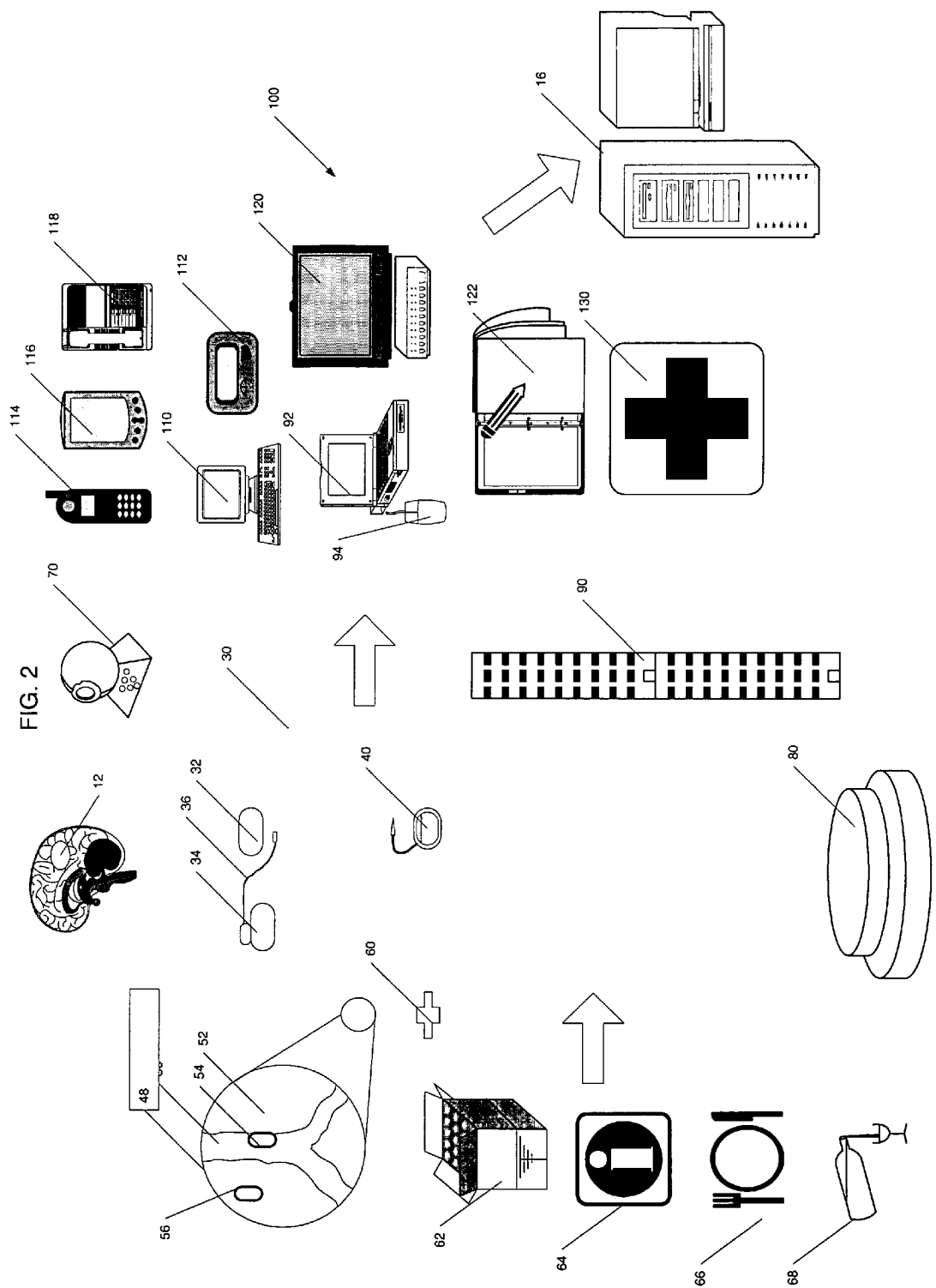
FIG. 2 is a schematic diagram illustrating various data collection and transmission components to provide information to a centralized data collection system.

FIG. 2 illustrates an individual patient 30 from the patient population 12 and their interaction with the central server 16. As previously indicated, a given patient is often a source of error in a clinical study for numerous reasons including, for example, inaccurate data reporting/collection, subjectivity, point in time measurements, and failure to comply. The present invention provides a number of mechanisms to reduce or eliminate this error.

In general, each patient 30 is provided with one or more implantable devices that collect data and that collected data is provided to the central server 16. In this manner that data may be collected at a greater frequency, is highly accurate, is objective, and aides in compliance issues.

FIG. 2 schematically illustrates a variety of components that may be utilized within the system 10, either alone or in various combinations. As indicated, each patient 30 will have at least one implanted device. By implanting the device, compliance is increased as compared to, e.g., a body worn monitor sensing the same parameter, which may be forgotten or deliberately left off during various situations.

There are various categories of implantable devices that are applicable to the present invention. In some cases, these implantable devices may be implanted solely for the purpose of conducting the drug study. In those instances, implantation should be minimally invasive for both patient safety and to encourage patient participation. Other implantable devices may be implanted for therapeutic reasons; that is, in addition to collecting data, these devices are capable or providing a medical therapy. Patient populations already exist that have such devices implanted. They may be relied upon for appropriate studies either by utilizing data already collected by these device or by providing or enabling additional data collection capabilities to these devices. In some cases, patient's participating in the study may be identified as candidates for these therapeutic devices and may receive implants accordingly.

Patient 30 is illustrated with a number of implantable device types and implant locations. As an example, a minimally invasive subcutaneous sensor 32 is implanted. The Medtronic Reveal® is an example of such a subcutaneous sensor. The Medtronic Reveal® is an implantable loop recorder that monitors electrical activity of the heart and records data into an internal memory. The data is telemetered to an external device for analysis. Sensor 32 illustrates the type of sensor (without limitation to the parameter(s) sensed) that may be implanted specifically for the clinical study. Also illustrated is an implantable medical device (IMD) 34. The IMD 34 may be, for example, a pacemaker, defibrillator, or combination device that senses electrical activity of the heart and delivers therapy in the form of high power electrical stimulation (defibrillation) and/or lower power electrical stimulation (pacing) through leads 36 coupled between the IMD 34 and the heart. The IMD 34 senses and records data that is telemetered to an external device and is also useful in the present clinical studies.

An implantable drug pump 40 is provided and may be completely implanted or include an external component. The drug pump 40 may be used to deliver a drug, including the drug under investigation, but may also include various sensing and data collection capabilities. A neural implant 42 is illustrated and is representative of devices that collect neural data and/or provide therapy such as deep brain stimulation, recordation of neural activity/EEG, nerve stimulation, drug delivery, and the like. While illustrated as implanted within the brain, it should be appreciated that all or a portion of such a device may be implanted in another anatomical location with either remote sensing of various parameters or the use of one or more leads that are implanted on or within the brain.

Within enlarged area 48, a portion of the patient's vascular structure 50 is schematically represented. Similarly, the patient's tissue structure 52 (muscle, fat, skin, etc.) is also schematically illustrated. Implantable sensors 54 and 56 generally represent components that may be injected or otherwise implanted with minimal invasiveness into these regions. The implantable sensor 54 may be attached to a specific location within a given vein or artery or alternatively, may move throughout the system with the corresponding blood flow or even under its own direction with an incorporated navigational and locomotion component. While the types and capabilities of such sensors will be described in greater detail, such a sensor may incorporate an RFID capability to both receive power for operation and to transmit data or may include an internal power source.

Thus, the patient 30 has at least one sensor implanted that collects data regarding at least one parameter and that data is provided to the central server 16. The particular type of sensor, implant location, and parameter(s) sensed will vary depending upon the nature of the clinical evaluation.

In addition to the implantable sensor, the system 10 may include a variety of external data collection mechanisms. For example, a wrist worn device 60 may be a sensor that collects any number of parameters such as blood pressure, temperature (patient, ambient), oxygen saturation levels, etc. In addition, the wrist worn device 60 may be a telemetric interface for one or more of the implantable devices. That is, the implantable devices may have a limited data transmission range and the wrist worn device may collect sensor data and either store it or re-transmit that data. Wrist worn device 60 is representative of any body worn or carried sensor and/telemetric interface such as a Holter monitor, sensor vest/shirt/belt/hat, or a device strapped to any portion of the body (e.g. about the chest).

In order to monitor compliance with the drug regiment, an electronic pill box 62 is provided within the system 10. The electronic pill box 62 senses when the patient 30 removes a dosage of the drug and reports that information. In addition, the electronic pill box 62 may include a communication interface that reminds the patient 30 to take the drug, when to take the drug, and the correct dosage. While illustrated as a "pill box" it should be appreciated that any form of the drug may be monitored whether pill, fluid, powder, inhaler or the like. The contents of the container are monitored; removal by the patient is noted; and an optional reminder may be provided. Other mechanisms for compliance with consumption of the drug may be provided. For example, each dosage may be provided with an indicator, e.g., an absorbable RDID tag that indicates consumption or detectable coating. Alternatively, one of the implantable sensors may sense ingestion of the drug or the presence and/or level of the drug in the patient's bloodstream, tissue, hair or other anatomical feature.

Any given patient 30 may have a large quantity of external data that is potentially relevant to the clinical study. This information is generically represented as external information input 64. The external information input 64 may include location data (e.g., GPS), environmental data (ambient temperature, external pressure, air quality), activity data (e.g. exercise equipment, GPS movement tracking/rate) or similar data. Various sensors may be employed to gather this information. In addition, while objective, sensed data is desirable; patient input and patient knowledge even if subjective can be collected. For example, patient observations of effectiveness, symptoms, side effects, activity, over the counter medications, and responses to clinician questions may be collected via information input 64.

Similar to both the electronic pill box 62 and the external information input 64, the patient's food 66 and liquid 68 may be relevant to the clinical study. As such, data regarding these parameters may be acquired. For example, with a strict diet regiment, prepackaged meals/drinks may have RFID tags or similar sensors that are activated via opening of the packaging or other patient action. Smart home appliances can detect the removal, use, processing and quantity of foods. Finally, the patient 30 can record the timing, type and quantity of food and liquid consumption.

Visual and audible data can be collected via one or more still or video cameras and microphones 70. Aside from traditional "videophone" communication with, e.g., a clinician, the camera and/or microphone 70 can monitor various objective parameters such as movement/activity, skin tone, coherency, breathing, snoring, stress (voice indicated) or the like.

Another category of input devices for the patient 30 includes external medical devices 80. Many such external medical devices 80 are similar in a number of ways to the above described information input devices 64. For example, one external medical device may be an electronic scale that transmits weight data regarding the patient to the system 10. Likewise, an electronic (external) thermometer that transmits patient temperature data would also be included in this category. The distinction between the external medical device 80 and information input device 64 is, broadly, whether the collected data is a patient specific data point or an environmental data point and there may be overlap. In addition, while not required, the external medical device 80 may also include therapy delivery capabilities. For example, an external device used to sense and record EKG data may also function as an automated external defibrillator (AED) or a glucose sensor may be coupled with an external insulin pump.

Thus far, various mechanisms have been discussed to generate data either via sensors, devices or patient input. This data must ultimately be provided to the central server 16. To facilitate this result, the system 10 includes a variety of interface options. One interface is a telemetry base station 90 that receives information from one or more sensors and communicates that information to another device. In one embodiment, the telemetry base station 90 is a reader post that provides RF energy to various RFID sensors on or within the patient 30 and collects the resulting transmissions. Such a reader post 90 may be a stand-alone device positioned within the patient's home and the patient 30 deliberately utilizes the device. Alternatively, such a reader post 90 (or multiple posts 90) could be positioned adjacent a doorway to a bedroom or restroom; thus, each time the patient 30 passes by the sensors are queried without deliberate effort by the patient 30. Similarly, the reader post could be positioned on or near a piece of exercise equipment, near an appliance, near (e.g., underneath) a couch, or in any convenient location. In addition to or instead of RFID, the base station 90 may communicate in a variety of other formats (e.g., Bluetooth) with the various sensors. For example, a given sensor may be self-powered and capable of RF transmission.

Similarly, an in-home monitor 92 that is similar to a medical device programmer such as the Medtronic Model 9790 Programmer™ or the Medtronic Model 2090 Programmer™ may be provided to interrogate one or more sensors. The in-home monitor 92 may utilize RF transmissions to collect data from a distance and/or may include a programming head or wand that is placed proximate the sensor and utilizes inductive coupling to communicate with the sensor(s). The in-home monitor may also utilize the base station 90 as a means to communicate with the sensors. Once collected, the data may be transmitted from the monitor 92 to the central server over any appropriate communication network such as a telephone line, Internet connection, satellite transmission, wireless network (analog, cellular, GSM, etc.) or alternative communication pathway. Of course, the in-home monitor may process certain information internally and provide feedback to the patient or take automated action.

While any external device (such as the external medical device 80) may include a direct communication link to the central server 16, in most embodiments, the implantable device will likely lack the capability to directly communicate with the central server. For space and power consideration, the implantable sensor is less likely to be equipped with a transmitter capable of directly accessing a wireless network (e.g., cellular, digital, GSM, GPRS, Internet, satellite, communication network, etc.) for direct communication to the central server 16. The present invention includes sensors capable of such direct communication, but also includes intermediary devices (collectively 100) such as the base station 90 and/or monitor 92 to act as a communication interface between the implanted device(s) and central server 16.

In addition to providing data to the central server 16, information may also be directed towards the patient or to one or more of the sensors (e.g., reprogramming, recalibration, etc.). Thus, the present invention includes a variety of intermediary devices 100 that provide data to the patient. For example, the monitor 92 may be utilized to program an implanted device or display an electronic message to the patient 30. Similarly, queries may be generated by a clinician and directed to a given patient 30, the patient population 12, or a subset thereof. The patients then provide responses to these queries that are collected at the central server.

Alternative intermediary devices 100 include a personal computer 110, pager 112, wireless telephone 114, PDA 116, standard telephone 118, or home appliance 120 (e.g., television, cable box). It should be appreciated that devices such as wireless phones 114 and/or PDAs 116 can be combined in functionality and may also include still or video communication capable of transmission of audiovisual information. Each intermediary device 100 may collect sensor data, provide that data to the central server 16, provide data to the patient (or to an implanted device), and/or receive patient responses. While not automated, traditional written communication 122 may also be provided to allow patient communication. Finally, a caregiver or clinician interface 130 is also represented. That is, the patient may physically travel to a clinician and have their implanted device interrogated by, e.g., a medical device programmer located at the clinician's office. This may be a clinician participating in the clinical study or a non-participating clinician the simply collects the data and provides that data to the central server 16. Clinician interface 130 also represents the traditional collection of data by the clinician, in office, such a lab work, medical history, and any appropriate medical evaluation with the results provided to the central server 16.

Figure 3:
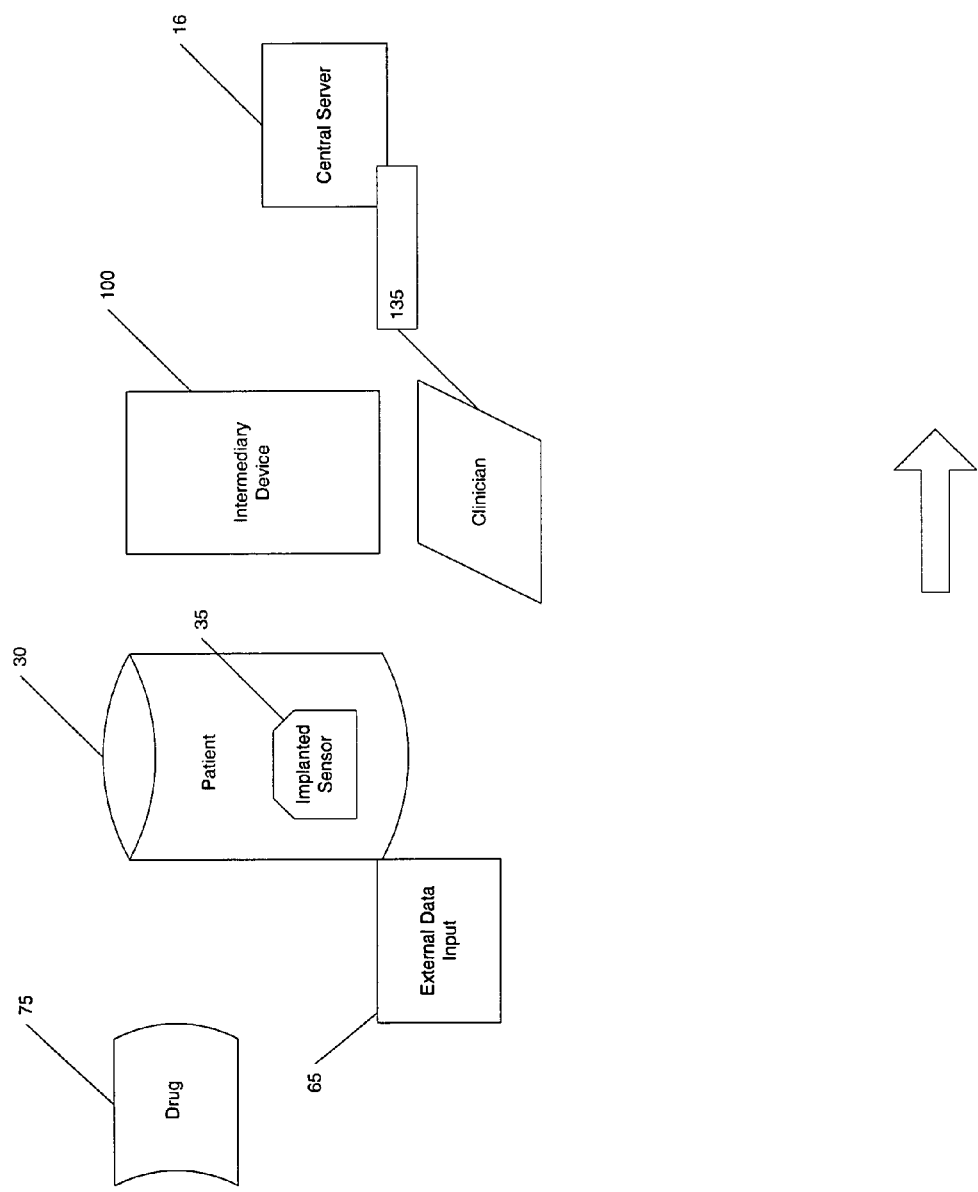
FIG. 3 is a block diagram that illustrates categorical groupings of the components from FIG. 2

FIG. 3 is a block diagram illustrating the above-described portion of the system 10. Namely, the patient 30 has at least one implanted sensor 35. A drug 75 under clinical investigation is provided to the patient 30 in an appropriate form. Various external data inputs 65 gather and provide data to the central server 16. One or more intermediary devices 100 interfaces with implanted sensor 35 (and optionally the external data inputs 65) and provides gathered information to the central server and also provides a communication interface between the central server 16 and the patient 30. The clinician 135 is responsible for the patient and may or may not participate in collection and transmission of portions of the data collected, depending upon the specific patient requirements. The portions of the system 10 utilized to collect, generate, process and manage data may be in one embodiment, those described in U.S. patent application Ser. No. 11/038,835, filed on Jan. 20, 2005, and is herein incorporated by reference in its entirety.

While not limiting nor exhaustive, the following table provides examples of implantable sensors 35 useful in system 10 that sense one or more parameters provided to central server 16 and also are capable or providing a therapeutic function.
Pacemaker/Implantable Pulse Generator (IPG)
Defibrillator
Implantable Cardioverter/Defibrillator (ICD)(Pacing and Defibrillation)
Implantable Drug Pump
Externally Worn Drug Pump
Neurological Stimulator (brain, nerve, spine)
Gastric Stimulator
Stomach Therapy Device—(nausea, hunger, obesity)
Gastrointestinal Therapy Device (Irritable Bowel Syndrome, constipation, incontinence)
Urinary/Bowel Control Device
Artificial Pancreas
Artificial Kidney
Stent Spinal Cage
Spinal Disk
Implantable loop recorder (pressure, rhythm)
Artificial Heart
Mechanical Heart Valve
Biologic Delivery Device
Ocular Implant
Insulin Pump
Chemotherapy Delivery Device
Radiation Delivery Device
Neuro-Cardiac Stimulator (vagal stimulation)
MEMS/Nanoscale Actuators (clot removal/destruction/retention)
Cardiac Potentiation Therapy (CPT) Device
Muscle Simulator (diaphragm, esophagus, skeletal)
Cochlear Implant
Cardiac Resynchronization Therapy (CRT) Device The following is a non-limiting, non-exhaustive list of implantable sensors 35 that may provide data to central server 10 alone or in combination with another device.

| | |
|---|---|
| Temperature Sensor | Lung Wetness/Edema Sensor |
| Heart Rate Sensor | Oxygen/Oxygen Saturation Sensor |
| Cardiac Output Sensor | |
| Cardiac Rhythm Sensor | Carbon Dioxide/Carbon Dioxide Saturation Sensor |
| Stroke Volume Sensor | |
| Ejection Fraction Sensor | Respiration Sensor |
| Pressure Sensor (Arterial, Venous, Endocardial, Epicardial, Pericardial, Respiratory, Renal, Gastrointestinal, tissue (e.g., aneurysm)) | Transthoracic Impedance Sensor (respiration and/or defibrillation, pacing threshold) |
| | Minute Ventilation Sensor |
| | C Reactive Protein Sensor |
| | Protein Sensor |
| Implantable External Pressure Reference Sensor | Elemental Sensor (N, Na, K, Cl, Ca, etc.) |
| pH Sensor | Position Sensor (relative body position) |
| Lead Position Sensor | |
| Lead Integrity Sensor | Motion/movement/activity Sensor (single or multi-axis) |
| Cardiac Contractility Sensor | |
| Vascular Dimensional Sensor | Location Sensor (GPS) |
| Vascular Integrity Sensor | Optical Sensor (visual, infrared, X-ray) |
| Vascular Topographical Sensor | |
| Cholesterol Sensor | Imaging Sensors |
| Blood Chemistry Sensor (T Cell, K, INR, glucose, creatine, BUN, BNP, ANP, troponin) | Acoustic Sensor (heart rate, heart rhythm, respiration, flow, thickness, viscosity) |
| Salinity Sensor | Doppler Sensor |
| Dimensional/Volume Sensor (Size, Shape, Position of Heart) | Partial Pressure Sensor (oxygen, carbon dioxide) |
| Rhythm Motion Sensor (Motion, Pattern, Modeling) of Contractual Cardiac Motion Sensor | Nitric oxide Sensor |
| | Ultrasound Sensor |
| | Ischemia Sensor |
| | Spectral Analyzer |
| Surface EKG Sensor (Subcutaneous, Device Mounted (e.g., "can")) | Nerve Conduction Sensor |
| | Stroke, Stroke Indicator Sensor |
| | Seizure Sensor |
| EGM Sensor | Enzyme Sensor |
| EEG Sensor | Serotonin Sensor |
| Neural Activity Sensor | Cellular State Sensor (e.g., cancerous) |
| DNA Analyzer/Sequencer | |
| RNA Analyzer/Sequencer | Cancer Marker Sensor |
| Fluid Viscosity Sensor | Noradrenaline Sensor |
| Fluid Flow Senor | Dopamine Sensor |
| Turbulence Sensor | Neurotransmitter (or surrogate) Sensors |
| Alcohol Sensor (blood, breath, cellular) | |
| | Neural Activity Sensor |
| Insulin Sensor | Hemorrhage Sensor |
| Glucose Sensor | Ambient/Environmental Sensor (light level, humidity, temperature, elevation, air quality) |
| Lactate Sensor | |
| Hormone Sensor | |
| Human Chorionic Gonadotropin (hCG) Sensor (Pregnancy) | |
| | Magnetic Sensor |
| Fertility Sensor | Hall Sensor |
| Estrogen Sensor | |
| Testosterone Sensor | |

-continued

| |
|---|
| Adrenaline Sensor |
| Drug Sensor (presence, concentration) |
| Nicotine Sensor |

The following is a non-limiting and non-exhaustive list of external devices (or the parameter monitored), such as information interface 64 or external medical device 80.
Scale (weight)
Height
Dimensional Measurements
BMI
Body Composition
DNA/RNA Sequencer
Blood Chemistry
Urinalysis
Blood Pressure
Glucose Sensor
Pulse Sense
Oximeter
Electronic Pill Box
Temperature (patient, ambient)
Biopsy
Microphone (voice data, respiration, heart rate/rhythm, snoring)
Patient Input (Quality of Life Data, symptoms, concerns, journal/log, compliance)
Imaging (video, still, infrared, X-ray, MRI, CT, PET)
EEG Sensor
EKG Sensor
Patient Identification
Patient activity (smart home technology e.g., time in bed, chair, amount of water, etc.)

Referring again to FIG. 1, each patient 30 of the patient population 12 has an implantable sensor 35 and a means to communicate sensor data to the central server 16. In addition, each such patient 30 may have the various external components and communication means described. As such, the system 10 provides a mechanism to objectively monitor a wide variety of parameters of a patient 30 participating in a clinical evaluation of a drug on a real-time, near real time, high frequency point in time basis, and/or on a critical need basis. In addition, such capabilities provide remote access to the patient while still permitting and/or providing in-office evaluation/consultation with a clinician.

Figure 4:
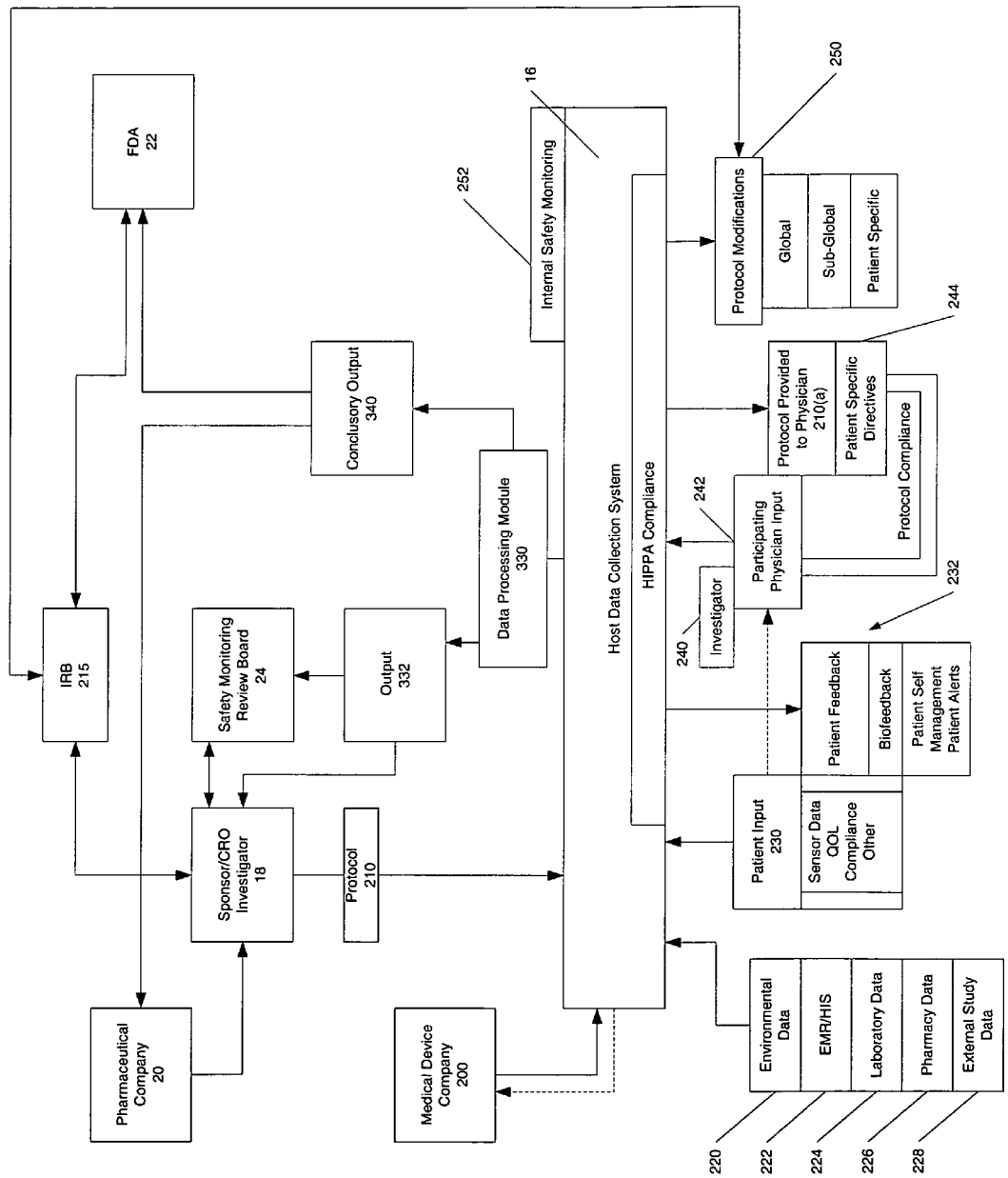
FIG. 4 is a schematic diagram illustrating the interconnection of various entities with the centralized data collection system.

FIG. 4 is a schematic illustration of the system 10. The central server 16 is referred to here as a host data collection system 16. That is, a given entity will provide the networking and interface capabilities and management to the sponsor 18. For example, information management companies and in some cases, existing medical device companies such as Medtronic, Inc. currently provide remote patient management and disease management capabilities, such as the Medtronic CareLink Network™. Such an established network is capable of communicating with various sensors and medical devices remotely, processing received data, and complying with various privacy practices and regulations with, e.g., a HIPPA Compliance module. The host data collection system 16 is therefore capable of processing data and protocols for multiple clinical studies simultaneously. New sensors and new types of sensor data are readily incorporated into the existing system to facilitate the requirements of any given clinical study.

An independent entity operating the host data collection system eliminates a perception of bias in the conduction the study. In addition, with a medical device company 200 likely to provide some or all of the implantable device, external devices, and communication interfaces their integration of those devices with a preexisting central server 16 provides for easier integration. While the host data collection system 16 is interchangeably referred to as central server 16, it should be appreciated that the host data collection system 16 could be spread over multiple components and locations. Furthermore, while benefits exist for using a host data collection system 16 created by and/or interfaced with a medical device company 200 that provides certain components, this is by no means a requirement or limitation.

As indicated, the system 10 is useful for preclinical investigation as well as for using the results thereof for generating a protocol based upon the preclinical work. In so doing, many of the components illustrated in FIG. 4 may be absent for the preclinical aspect. That is, the pharmaceutical company 20 or researcher may interface directly with host data collection system 16 to conduct the preclinical work and/or download a module from the host data collection system to perform or manage the preclinical work on servers/terminals under the control of the pharmaceutical company 20.

As an illustration, the system 10 of FIG. 4 will be described with respect to a clinical trial, with the understanding that the system 10 may be used, without limitation, for research, preclinical, Phase I, II, III and post market surveillance as well as for other investigational aspects.

The pharmaceutical company 20 has developed a new drug BPX and a sponsor 18 believes BPX will be effective in treating hypertension. As such, the sponsor intends to submit an IND application to the FDA and conduct clinical trial to evaluate BPX in humans.

Figure 5:
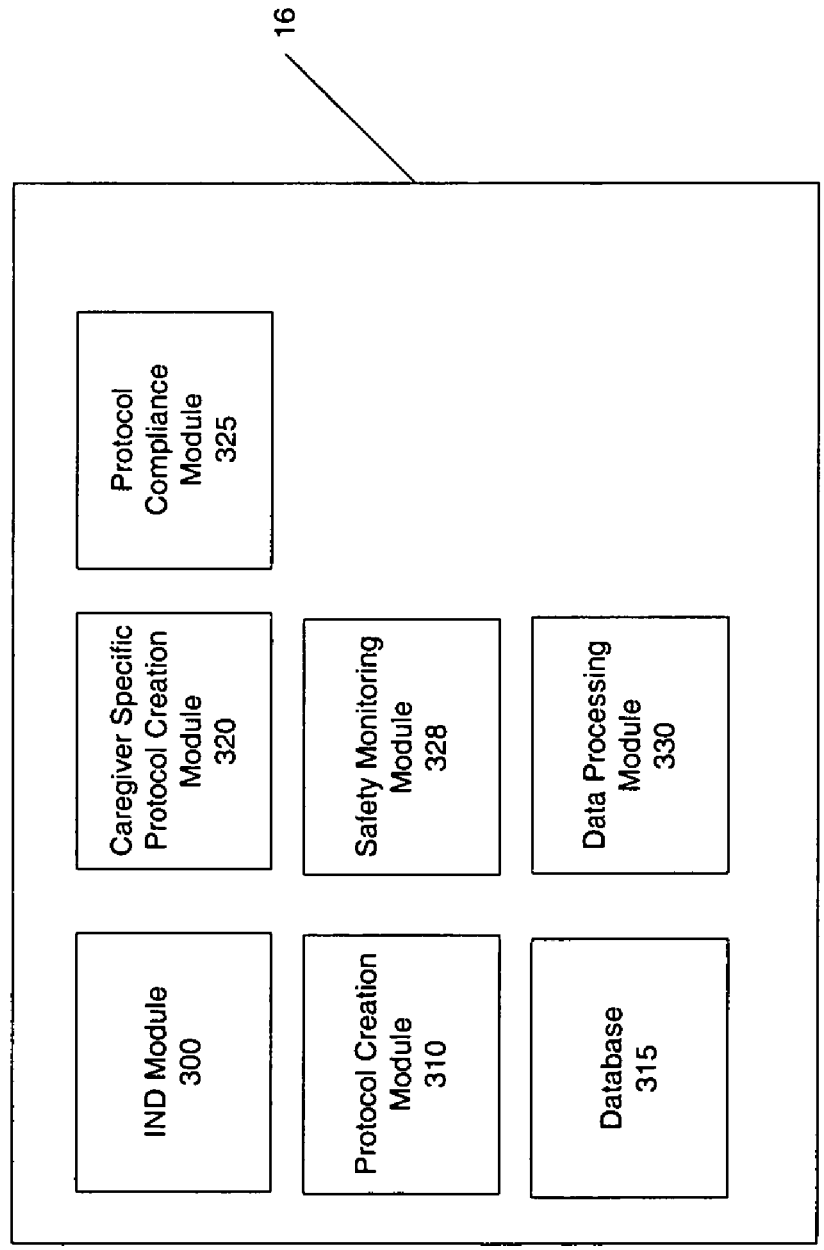
FIG. 5 is a block diagram illustrating some of the software and/hardware modules of the host data collection system.

In preparation of submission of the IND, the sponsor 18 creates or accesses an existing account on the host data collection system 16. An IND module 300 (FIG. 5) within the host data collection system is accessed and permits the sponsor 18 to prepare an IND application. It should be appreciated that the various modules described herein may be accessed remotely (e.g., via a web interface), software may be downloaded onto the sponsor's computer, or a combination of the two may be utilized.

The IND module 300 periodically interfaces with the FDA 22 to electronically update the filing and content requirements for an IND application. While the specific requirements for such an application will vary depending upon current FDA policy as well as the type of drug, the IND module 300 will generally prompt the sponsor 18 for animal pharmacology and toxicology study results, alternative human study data (e.g., studies from a foreign countries, human trials for other treatments, etc.), the composition of the drug, the manufacturing process, as well as the qualifications and controls employed by the manufacturer.

In addition, the IND application will include the protocol 210 to be employed in the clinical trial. The host data collection system 16 includes a protocol creation module (PCM) 310. The PCM 310 helps the sponsor 18 to acquire the required information (e.g., pulling from appropriate electronic files/databases, indicating a physical location of the information, etc.), format the data accordingly, suggest variables based upon data currently provided by the sponsor 18 and generate a protocol 210. The PCM 310 will generally request an identification of the primary and any secondary objectives of the study. The PCM 310 will also include an identification of the patient profile that will be selected to participate. The treatment parameters including duration, dosing, baseline comparisons, whether the trial is blind, double-blind, etc. and the measures taken to implement this aspect, a description of the safety protocols that will be employed, expected complications and any resulting action taken (including what would justify termination of the study), and methods of data collection, quality control and statistical analysis. In addition, the PCM 310 will prompt for the qualifications of the sponsor, the investigator(s), and the specific of the trial site or trial sites in a multi-site study.

The PCM 310 will evaluate the content of the data submitted, suggest alternatives based upon successful applications, and highlight potentially dangerous aspects (e.g., proposed dosing will in excess of toxicity established during pre-clinical work, comparing the current drug to similar drugs previously tested in the database).

Ultimately, the sponsor 18 will have control over the final contents of the resultant protocol 210. The sponsor 18 indicates which IRB 215 the protocol 210 will be submitted to for approval. The host data collection system 16 provides the completed protocol 210 and any additional selected information to the IRB 215. The IRB 215 is an independent body tasked with reviewing the safety of appropriate handling of patients involved in the study. The IRB 215 may approve, deny, or suggest modifications required for approval of the protocol 210. This decision is then supplied to the host data collection system 16. Approval or denial is reported to the sponsor 18. If the IRB 215 suggested modifications, those suggestions are communicated to the sponsor 18 and the host data collection system 16 will generate a modified protocol 210 based on those changes requested by the IRB 215 for consideration by the sponsor 18.

When the IRB 215 ultimately approves a protocol 210, the sponsor 18 will initiate the appropriate phase of the study. This may involve coordinating with multiple sites and multiple caregivers and will include identifying and selecting a sufficient number of patients for the study.

Based upon the nature of the "drug" and the aspects of the protocol 210 the sponsor may request and/or the host data collection system 16 may suggest certain patient parameters to monitor and the various mechanisms available to collect that data along with the advantages and disadvantages of each. For example, the illustrative drug BPX is intended to control hypertension. Thus, blood pressure data will be collected. Implantable pressure sensors may be identified; external home sensors may be identified; or traditional caregiver evaluation (or any combination thereof) may be suggested or required. Cost, ease of use, nature of implant (if applicable), reliability, patient/caregiver burden, and similar factors can be considered.

The measurement of patient's blood pressure in the trial is an obvious example of a necessary parameter that would indicate efficacy. Of course, the drug could increase hypertension or cause hypotension and thus this parameter would also be indicative of a symptom, event or adverse reaction. The drug could cause unrelated physiological effects that might become apparent through monitoring, such as abnormal EKG. Depending upon the phase of the trial, the known effects of the drug, and various other experiences or insight, certain other parameters may be indicated for remote monitoring. It should be appreciated that as the trial progresses and more issues materialize, these considerations can be reevaluated and remote-monitoring capabilities can be added or removed.

For purely illustrative purposes, a variety of remote monitors may be applicable to an evaluation of BPX in treating hypertension. For example, the Medtronic Reveal™ may be implanted to collect and record cardiac EKG data. Thus, if BPX causes any adverse effect on cardiac performance, such an effect will be noted. This is particularly beneficial if the symptom is not continuous. For example, shortly after BPX is ingested, after fully absorbed, or some time after absorption, the drug may cause a dangerous but transient arrhythmia. Thus, sporadic monitoring in a clinical environment may never sense such an effect. In addition, the reaction may only occur when one or more other variables are met. For example, the BPX only causes the arrhythmia if taken within an hour of taking particular pain reliever; thus, making it even more unlikely that intermittent in-clinic monitoring will identify the issue. Even if an event were recorded, repetitive testing may fail to show another arrhythmia absent the other variable (e.g., pain medication).

Of course, the patient (assuming hypertensive) may be prone to cardiac conditions and even if not caused by BPX, detection and treatment of such a condition would be of obvious benefit to the patient. Similarly, while BPX is being studied for its effects on hypertension, it may very well have a positive effect on cardiac conditions. For example, perhaps BPX unexpectedly reduce or reverses some aspect of heart failure that point in time measurements may not clearly indicate whereas continual evaluation by the implantable device reveals the trend. Depending upon the patient population in the current study, the protocol/IND application could potentially be modified to include an evaluation of BPX for the treatment of heart failure. More likely, the same or a new sponsor could begin a new trial for use in this area.

Continuing with the examples, BPX may be known to or suspected of affecting respiration in some patients. Thus, an implantable, impedance based minute ventilation sensor might be provided. Alternatively, an implantable oxygen sensor could be employed to monitor oxygen saturation.

Finally, there may be a known or anticipated, serious risk imposed by BPX that can be mitigated by a prophylactic medical device to such a degree as to render a protocol approvable based upon a patient risk assessment. For example, BPX may be known or believed to cause ventricular fibrillation is some cases. Thus, patients in the study may be provided with an implantable medical device, such as a subcutaneous ICD (implantable cardioverter defibrillator). The subcutaneous ICD is minimally invasive and provides the prophylactic protection required to safely conduct the study.

In addition, the various external monitoring equipment is established for the patient population 12. This may include a standardized specification as part of the formal protocol 210 or the sponsor's 18 requirements. In addition, certain equipment may be optional based upon patient criteria. For example, patient compliance may be a greater concern for a given group of people for any number of reasons. Particularly active/busy individuals may be more likely to forget; elderly patients may have memory concerns; younger patients may tend to be less responsible justifying additional devices, in some instances. These are, of course, very broad generalizations that may or may not apply. Thus, such categorical requirements can be defined by the sponsor 18 or simply made based upon an analysis of each patient. Where a concern, an electronic pill box 62 or other compliance mechanism may be provided.

The host data collection system 16 includes or has access to one or more databases 315. Of course, the host data collection system 16 is responsible for collecting, storing and processing the data gathered remotely from the participating patients 12. In addition, the host data collection system 16 may have access to past clinical study data, concurrent clinical study data, patient electronic medical records (EMR), health information systems (HIS), and external information resources (e.g., Internet). Thus, depending upon patient privacy limitations, the host data collection system 16 may assist in the identification of potential participants in the clinical study.

After approval of the protocol 210, the sponsor 18 begins to enroll appropriate patients 12 in the study. An appropriate investigator 240 evaluates each patient 30 in compliance with the protocol 210. Any necessary testing or screening is performed and assuming the patient 30 qualifies, is given a supply of the drug, a placebo, or an alternative drug. A medical history is taken and the data is provided to the host data collection system 16. Each patient 30 is implanted with one or more sensors and/or medical devices 35, provided with any external devices 65, provided with any intermediary devices 100 and enrolled in the host data collections systems 16 to enable remote data collection.

For any given patient 30, the host data collection system 16 can receive data from a number of sources. For example, environmental data 220 can be collected and stored. Such data may include current air quality, seasonal data (e.g., pollen counts), or external events (fires, eruptions, temperature, humidity, etc.). A remote sensor may sense similar environmental data; however, this category 220 is based upon data collected from informational sources (e.g., weather web sites, news and information web sites/databases, etc.) based upon patient location.

If available and provided appropriate legal access and patient consent, the host data collection system 16 interfaces with all available electronic medical records/health information systems 222 that contain patient 30 data. Thus, while the study operates according to its protocol, the patient 30 may be seen by any number of caregivers for any number of reasons including preventative care, disease management, and acute care. This data is incorporated into the profile for the patient 30 on the host data collection system 16. As such, events, reactions and occurrences that would be unexplainable based solely upon the monitoring of the investigator may be fully understood in the context of the patient's complete medical care. Similarly, data regarding a given patient 30 is electronically gathered from laboratory databases 224 and pharmacy databases 226. For example, a patient 30 may forget (or deliberately withhold) that they are taking a given medication or the patient may begin taking that medication subsequent to their participation in the clinical trial. In any event, the knowledge that this medication is being taken by the patient 30 may be very important in the evaluation of the drug and could otherwise go unnoticed. Furthermore, depending again upon patient consent and a given pharmacy's data tracking, even non-prescription purchases may be noted and provided to the host data collection system 16 for the same and similar reasons. Finally, the host data collection system 16 also incorporates external study data 228. This includes published data from studies external to the host data collection system 16 but also to concurrent studies occurring within the host data collection system, again subject to privacy and ethical regulations.

Each patient provides his or her patient input 230 to the health data collection system 16. This includes the remotely collected sensor data (implanted and external), the collection of which is often transparent to the patient 30. The patient 30 provides other types of information through the intermediary device 100 to the host data collection system 16. For example, the central server 16 on an automated bases, the investigator on a global basis, or the investigator on a patient specific or subgroup basis, may generate questionnaires regarding, e.g., quality of life issues. Thus, responses to such questionnaires are submitted to the host data collection system 16. Direct reporting of concerns or symptoms can be provided via, e.g., email communications, facsimile transmissions, voice transmission or the like directly to the host data collection system either as initiated by the patient 30 or according to a predetermined schedule.

Based on the data collected, the investigator 250 or the host data collection system 16 may provide feedback 232 to the patient 30. Such feedback may be a response to patient questions, an indication to alter a behavior (e.g., decrease dosage), a reminder to take the drug, or to call, send or otherwise provide information as requested. Likewise, the feedback 232 may include biofeedback to help with compliance of the management of a condition. For example, data may indicate an increase in blood pressure in response to the consumption of particular foods, thus the feedback includes 232 such information. Alternatively, as the system 10 notes an increase in blood pressure, such information is provided the patient 30 allowing them to note the current condition and alter their behavior, such as ending a stressful situation or stopping their current consumption of a particular item.

The investigator 240 is illustrated in conjunction with a participating physician 242. This is meant to illustrate that at any given site participating in the clinical study, there will be an investigator 240 (who may even be the same entity as the sponsor 18). The investigator serves multiple roles in that they are responsible for complying with the protocol 210 but may supervise other physicians 242 or caregivers such as nurses, technicians and the like. Thus, the grouping of caregivers 242 is following the protocol 210, may have interaction with the patient 30 and may collect or generate data that is provided to the host data collection system 16.

In doing so, the participating physicians 242 receive the current protocol 210(a) from the host data collection system 16 that may include specific directives 244 for the patient 30, based on that patient as an individual or as a member of a subclass of the patient population 12. For example, the protocol may require a specific test for all participating male patients over the age of 60. The protocol 210(a) is provided to the participating physician in a manner that provides a clear indication of the steps to be taken for a current evaluation of the specific patient 30. That is, rather than assuming a given participating physician 242 (or any caregiver) is familiar with the overall protocol 210, the relevant portions of that protocol 210(a) are provided in an appropriate manner based upon the caregiver as generated by a caregiver specific protocol generation module 320 residing on the host data collection system 16.

As one example, perhaps a laboratory technician screens hundreds of patients per day and routinely draws blood for testing. The protocol 210 may require a particular sequence or particular action that may vary from this laboratory technician norm. Thus, the protocol provided 210(a) may be a very direct, step-by-step list of instructions in an order to perform to each step. Alternatively, the protocol 210 may require that during the taking of a medical history on a six-month date on the study, data relating to the patient ability to interact socially should be obtained. For a physician 242, the protocol 210(a) may be a directive to gather such data without providing specific "step by step instructions." That is, it may be more beneficial to let the caregiver determine the means of acquiring the data most accurately based upon their skill, education and training than attempting to dictate a set of instructions for every situation. The host data collection system 16 thus provides appropriate portions 210(a) of the protocol 210 to the relevant caregiver 242, at the appropriate time and in the appropriate context.

As the context specific protocol 210(a) is provided to the participating physician 242, the host data collection system 16 expects certain responses to be returned. Thus, whether these responses are received and to what degree they are complete permits the host data collection system 16 to monitor the participating physician's compliance with the protocol 210. This operation is performed via a protocol compliance module 325 residing on the host data collection system 16.

In addition to determining whether specific data is provided and provided correctly at a specific time, the protocol compliance module 325 evaluates all data related to the clinical study and identifies various irregularities or discrepancies. For example, two different caregivers participating in the study may routinely see a given patient 30 and the data they collect may frequently differ unexpectedly. This may indicate a problem with the method or means of data collection or illustrate the introduction of subjective interpretation errors. Similarly, patients 12 at one site may routinely have data that is skewed as compared to patient populations at other sites. The protocol compliance module 325 can detect and process such variations early on and, if possible correct or suggest corrections to the sponsor 18 to ensure the quality of the study. This may indicate compliance issues with the caregivers, patients or even the manufacturer. For example, a given "lot" of the drug may be problematic and the host data collection system 16 can help identify this as an explanation for clustered symptoms based upon a tracking of the drug supply.

During the course of the study, the sponsor 18 may desire to change the protocol 210. Such a change may be based upon data provided by the host data collection system 16. The change to the protocol 210 is offered through the host data collection system 16 to the IRF 215 for their approval. Assuming it is approved, the protocol modifications are incorporated by the host data collection system 16 as the protocol 210 and provided to the various participants, efficiently and globally. The protocol modifications 250 could apply to the entire protocol 210 or just affect a subset of the patient population. The system also permits the recipient to acknowledge receipt of the modification. As indicated, a modification may also be patient specific. This would more likely be reflected as a variance from the protocol 210 rather than a modification of protocol 210. The guidelines for conducting clinical studies require that such variances are reported and explained; the host data collection system 16 provides that capability in this context.

The sponsor 18 employs the safety monitoring review board 24 to monitor the study and evaluate preliminary data and protocol compliance to ensure patient safety. As such, the host data collection system 16 is accessible to and provides appropriate information to the safety monitoring and review board 24.

In addition, the host data collection system 16 provides an internal safety monitoring function 252 via a safety-monitoring module 328. The safety-monitoring module 328 evaluates the collected data along with an output from the protocol compliance module 325. If the safety-monitoring module 328 determines that there is a risk to patient safety, (specific patient, patient group or type of patient) then the host data collection system 16 can respond. If the risk is speculative or mild, the sponsor 18 is alerted 18. If the risk is severe and urgent, the sponsor 18 is again alerted, but in an active manner. That is, rather than generating an electronic message which may be reviewed at an indeterminate time, the host data collection system 16 calls or pages the sponsor 18 or otherwise assures short term notification. This may be done in an automated fashion or an operator working with the host data collection system 16 may undertake the task. Again, depending upon severity, the host data collection system may notify the investigators and/or the IRB of the potential safety issue along with any recommendations. For example, behavior may be modified, the study terminated or caregivers may be advised to follow their patients more rigorously for a period of time. Whether the host data collection system 16 communicates directly with patients 12 would depend upon the severity of the issue detected and the authority provided to the system 10 by the sponsor 18.

The safety-monitoring module 328 provides a verification process as well. That is, the data collected is analyzed within the host data collection system 16. The sponsor 18 will ultimately control the data, the methods of analysis, and the conclusions drawn; however, in the unlikely event a sponsor 18 or investigator 240 either intentionally or inadvertently misrepresents or manipulates the data or takes measures that are unsafe to one or more patients to obtain more favorable data, the safety monitoring module 325 provides the raw data and/or independent analysis to the IRB 215 and/or FDA 22.

As the host data collection system 16 collects data, a data processing module 330 statistically analyzes the data and provides the results as well as any data requested to the sponsor 18 on a real-time or near real time basis as output 332. Of course, the sponsor 18 may elect to receive such data and/or analysis on a less frequent basis. Upon conclusion of the trial, the complete data set in analyzed according to the parameters of the protocol 210 and is represented as conclusory output 340. This data typically is the resultant work product of the sponsor 18. Thus, the sponsor 18 manages the conclusory output 340. That is, additional or different statistical analysis may be performed before finalizing the results. In the end, the approved conclusory output and any accompanying reports are submitted to the FDA 22 for approval. It should be appreciated that the FDA is merely exemplary and the present invention is applicable to various governmental, regulatory and institutional bodies for any number of reporting purposes. Similarly, the system can prepare and format data for the foreign counterparts of these entities.

To the extent desired, this same data may be provided to the pharmaceutical company by the system 10. Of course, the data may be presented in the form of a paper for submission to a journal for publication and peer review. The host data collection system 16 modifies and formats the conclusory output, permits sponsor 18 input and modification, and suggest additional material to include in generating the paper for submission.

Assuming that the conclusory output 340 leads to a determination of appropriate safety and efficacy, the host data collection system 16 can generate a New Drug Application (NDA) for submission to the FDA. The NDA would include required information from the clinical study and the conclusory output 340 and may include information from the pharmaceutical company 20 and/or sponsor 18. The FDA then reviews the NDA and may approve the drug for use according to particular labeling requirements.

Figure 6:
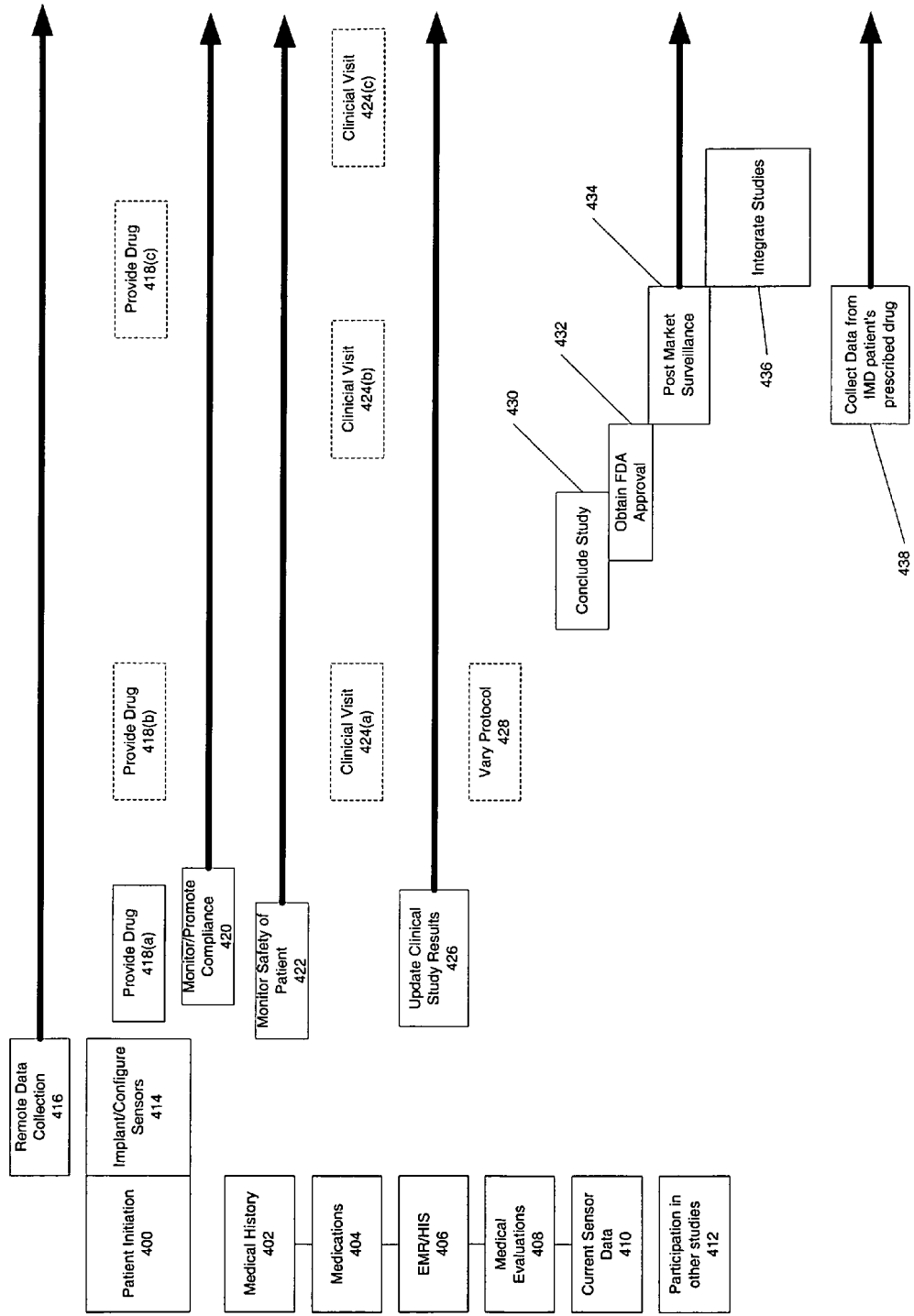
FIG. 6 is a schematic diagram illustrating a timeline of the process involved with utilized the system for clinical study data collection and processing.

FIG. 6 is a flowchart illustrating a temporal relationship between various actions taken when utilizing system 10 to conduct a clinical study of a new drug. Drug as used herein means any controlled substance, pharmacological, biological, biomedical, pharmacological, or organically derived agents, compositions or compounds. While such drugs are typically used in the treatment, management, inhibition or prevention of a disease, symptom, condition, or other malady; the term "drug", as used herein, means any such substance that requires FDA approval. It should also be appreciated that the FDA or other government regulating body may require similar approval for devices or medical technology, particularly when used in combination with a drug. The present system is capable of monitoring parameter for any or all of these categories, alone or in combination.

A given patient 30 is evaluated for initiation (400) into the trial. Appropriate information is collected and reviewed to determine if this patient 30 meets the criteria set forth in the protocol 210 for eligibility in the study. The investigator 240 or a caregiver under his direction takes a medical history (402) of the patient; identifies the patient's current medication regime (404), accesses the patient's EMR/HIS records and reviews (406) their content; conducts any appropriate medical evaluation of the patient (408) (e.g., blood tests, X-rays, etc.), and identifies any currently implanted or available external sensors monitoring patient activity (410). That is, the patient 30 may already have an implanted device, such as an ICD capable or collecting and remotely providing data that may be useful to the system 10. Such availability may or may not be a screening criterion for participation in the clinical trial. Finally, the investigator 240 determines whether the patient 30 is currently participating in any other clinical trials (412) and/or whether the data collected from this patient 30 may be useful for an alternative study. If so, patient consent may be requested to utilize the data for multiples studies. The information collected and access to available electronic records (e.g., EMR) is provided to the host data collection system 16.

One or more implantable sensors is provided and configured (414). This would include implanting new sensor(s) or utilizing an already implanted sensor or device. The use of an already implanted device may be straightforward or require reprogramming of the device to obtain desired data. Any external sensors or devices are provided and configured. Once established, data collection (416) from the remote sensors begins on either a continuous or appropriate intermittent (e.g., point in time measurements) basis. This would entail storage of data in the sensor/device and/or transmission of the data to the host data collection system 16 either directly or through one or more intermediary devices.

Once the patient 30 is appropriately screened, entered into the study, evaluated, and provided with the appropriate sensors, the patient 30 is given (408($a$)) the drug. This would include the drug under investigation, an alternative treatment option, or a placebo. As indicated, the drug may be provided (408($a$)($b$)($c$)) multiple times. The nature of providing the drug (408) and the frequency of providing the drug depend on the drug itself and the requirements of the protocol 210. For example, a supply of drugs in pill form may be provided to the patient 30 and then "refilled" on subsequent visits to the investigator (as necessary). An investigational drug may be new to the market and if so, would not be available by prescription and filled by a pharmacy; however, if the study involves utilizing an already approved drug for a different purpose, then the patient may be able to acquire the drug from a pharmacy to participate in the study. Alternatively, the nature of the drug or its method of delivery may require that the investigator deliver the drug to the patient 30 for each dose.

The system 10 will monitor the compliance (420) of the patient 30 in taking the drug according to the protocol 210. This can occur as described above via, e.g., patient reporting, electronic pillboxes or other sensing means, or by investigator 240 designation if delivered directly to the patient under the supervision of the investigator 240. As indicated, patient compliance (420) is monitored on an on-going basis during the study. In addition, the system 10 may continue to monitor compliance after the study for post market surveillance purposes.

The safety of the patient is monitored (422) upon initiation of data collection and the patient's taking the drug. Safety monitoring (422) is performed by the host data collection system 16, the caregivers conducting the study, alternative caregivers the patient may see, and all such data is collected. The IRB 215 in effect monitors patient safety prior to initiation of the study by assuring that the protocol 210 provided is appropriate and that the sponsor/investigators are competent. Patient safety monitoring (422) as temporally indicated refers to the ability of the system 10 to perform this function and collect relevant data.

As indicated, the host data collection system 16 receives data and is capable of processing and analyzing that data. In that regard, the "results" (426) of the clinical trial are being processed/updated as soon as the host data collection system 16 begins to receive data. Of course, this occurs on an on-going basis until the study in concluded (430) and the final analysis is performed.

During the course of the study, the patient 30 is seen (424 (a)(b)) by the investigator 240 (or caregiver under his direction) for evaluation. In addition, the patient 30 may be seen after the conclusion of the study (424(c)). Whether and how frequently these evaluations occur is established by the protocol 210 and/or patient need. If during the course of the study, the data suggests that a change is warranted, the protocol 210 may be varied (428) as described above.

Upon conclusion of the study, the results are submitted with a New Drug Application to the FDA for market approval (432). Assuming such approval is granted, physicians may then prescribe the drug accordingly. As this occurs, a patient population utilizing the now approved drug will develop. Post-market surveillance (434) is conducted and over time, new attributes of the drug may be noted. That is, long term usage, variances in dosing, drug interactions, or other issues may reveal side effects or other consequences (that may be either positive or negative) of utilizing the drug. Such data is collected and reported, and if warranted, the approval of the drug may be modified or retracted.

Such post-market surveillance (434) currently occurs on a generally ad-hoc basis. That is, if issues arise in sufficient number or otherwise become readily apparent, a connection to the drug may be drawn. The present invention provides a greatly improved post-market surveillance capability.

The host data collection system 16 collects data for the studies as indicated. In addition, in certain embodiments, the host data collection system 16 collects patient data remotely for other purposes, such as monitoring the performance of an implanted medical device. As the population of patients taking the approved drug grows, the number of those patients who are monitored by the host data collection system 16 will also grow. This would include patients involved in the study who continue to receive the drug, post approval as well as those patients monitored (438) for some other purpose who are prescribed the drug.

Within the limits imposed by patient privacy rights, the host data collection system 16 provides a robust post market surveillance feature in that the entire population of monitored patients and access to either some or all of their medical records permits potential issues with the drug to be identified. This is based on the data collected (436) post market as well as data obtained from medical databases related to other studies; subsequent studies done that provide comparative data on other drugs and/or where study participants are also using the now approved drug; and subsequent studies done of the same drug for the same or alternative uses.

The practical limitations of a clinical trial limit the time permitted, the number of patients involved and of course the number of variables that can be evaluated. Any given patient will have a unique set of parameters and no drug may be practically evaluated against every possible set of parameters. However, in post-market surveillance via the host data collection system 16 and the system 10, each participating patient is monitored with their unique set of parameters.

When a participating patient is given the new drug, the host data collection system 16 collects data from available sensors and permits an automated analysis to be prepared and provided to the patient or the patient's caregiver. As data is collected, trends can be established and consequences may be predicted before they cause substantial harm. For example, a medical device may monitor an indicator of a disease state such as cardiac pressure or pulmonary edema as an indicator of heart failure status. A given heart failure patient may start taking the drug and the host data collection system 16 may detect an increased upward trend in e.g., pulmonary edema that correlates with taking the new drug or a dosage change in the new drug. Thus, the system 10 can indicate that the new drug may be causing this effect and provide this data to the caregiver. Once alerted to the potential problem, the caregiver may take the patient off of the drug. The results may indicate that the drug was likely the source of the problem or if the problem continues, negate that inference. In either case, additional data has been collected regarding the drug. Of note, without the monitoring the problem may have progressed slowly and over time to a critical state and required significant intervention. As the focus at that time would more acutely focused (e.g., lifesaving techniques) the correlation with the drug may easily have been overlooked or difficult to establish scientifically and reliably.

The effect of such a direct correlation of taking the drug to a patient reaction is one example of how the system 10 can continue to provide post-market surveillance. In addition, with a robust monitored population, there will likely be multiple patients having similar sets of parameters. For example, there are a vast array of available prescription drugs and the likelihood of any given patient having multiple ailments and hence many prescriptions for those ailments is high. Conversely, the odds of finding comparable complex patients on comparable complex drug regiment who begin taking the new drug is relatively low. The odds of identifying an interaction between the new drug and one of the patient's medications or conditions in isolation is also low; as is the likelihood that disparate caregivers could connect the similar patients. However, with the host monitoring collection system 16, all of this data is collected and processed for exactly these types of interactions. Thus, when an adverse reaction occurs or trend information indicates an adverse reaction, the system 10 will note the relationship.

Single drug interactions are relatively simple; for example, the system 10 may note that any patient taking a beta-blocker will have an adverse reaction when given the new drug. More complexity is involved when patients have an adverse reaction only when taking a beta blocker, but only in a certain dosage range, in combination with a blood thinner, in combination with a specific cholesterol drug, who smoke and are overweight. Again, by monitoring these variables over a broadening patient population, the system 10 provides a mechanism to make connections between patients for a robust post-market surveillance for the drug in question.

While the above is meant to illustrate the benefit to medical community by providing more accurate and tailored labeling, use, interaction and cautionary information (or perhaps indicating that the drug should not be used at all), the system 10 also provides a more direct benefit to the patient. That is, while improved overall drug surveillance in the market benefits patients, the system 10 can provide direct feedback to a specific patient (alone or in the context of developing this body of knowledge relating to the drug). For example, while a given drug may be extremely safe for the vast majority of patients, a given patient may have a specific adverse reaction. The system 10 can alert the patient to warn them that an adverse trend is occurring; that an adverse event is occurring that might otherwise be imperceptible (e.g., certain arrhythmias, increased cholesterol levels); or to summon an emergency response automatically if a sever adverse reaction occurs.

Similarly, specific patients and the medical community in general benefit from a biofeedback type response provided to the patient. That is, the above description has generally been related to adverse reactions. The system 10 can monitor variables indicative of effectiveness as well. Thus, a specific patient may reduce the effectiveness (or generate an adverse reaction) when eating specific foods, drinking particular liquids or engaging in particular activities. In a fully monitored patient, the system 10 may be able to determine the substance or activity reducing effectiveness. More likely, the system 10 can alert the patient when effectiveness is reduced and request input as to the patient's current and recent activities/consumption. These effects and the benefit of the drug may also vary depending upon the dose of the drug. Thus, the drug dosage and patient activities are individually tailored to the patient based upon their specific parameters. Furthermore, over time these requirements may change and this patient customization can occur on an on-going basis via system 10.

The present system is useful for clinical investigations and post market surveillance. By providing robust monitoring, the number of patients required to obtain meaningful results can be dramatically reduced as compared to traditional studies. Conversely, larger numbers of patients, if enrolled, are more easily and accurately managed. This process allows manufacturing to tailor more targeted drugs and test in the appropriate subject of patients, which would otherwise be impractical. Furthermore, as the present invention gains acceptance, certain drugs may be "pre-approved" if utilized with robust monitoring. That is, the reliability, safety and efficacy of the monitoring may allow the FDA (or other agency) to conditionally approve a drug prior to a full clinical study knowing that the appropriate patient monitoring is in place. Thus, providing drugs became available faster and data is still collected and evaluation. Regardless of FDA process and safeguards, the present invention permits manufacturing to monitor the safety and efficacy of other products beyond the mandated standards of the regulatory bodies.

The preceding specific embodiments are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than is specifically described, without departing from the scope of the present invention. As to every element, it may be replaced by any one of infinite equivalent alternatives, only some of which are disclosed in the specification.

The invention claimed is:

1. A system comprising:
    means for receiving a protocol for conducting a clinical study of a drug;
    an implantable sensor for collecting study data from a plurality of patients enrolled in the study;
    means for receiving the study data remotely from each of the plurality of patients enrolled in the study;
    means for processing the received data according to the protocol to generate a conclusory output indicating a result of a current phase of the clinical study;
    means for evaluating a response to an intake of the clinical trial drug of each of the plurality of patients based on the processed data;
    means for developing a trend of a disease state for each of the plurality of patients based on the response;
    means for predicating the occurrence of an adverse effect based on the developed trend;
    means for evaluating patient safety based on the prediction of the occurrence of an adverse effect;
    means for evaluating the risks to patient safety;
    means for providing feedback to the patient based on the evaluation of the risk patient safety; and
    means for determining the mode of the feedback to the patient based on the evaluation of the risk to patient safety.

2. The system of claim 1, further comprising:
    means for interfacing with a study sponsor; and
    means for interactively generating the protocol with the study sponsor via the means for interfacing.

3. The system of claim 1, further comprising:
    means for generating an investigational new drug application that includes the protocol; and
    means for communicating the investigational new drug application to an investigational review board for submission.

4. The system of claim 3, further comprising:
    means for receiving data from the investigational review board; and
    means for modifying the protocol based upon the data received from the investigational review board.

5. The system of claim 1, further comprising:
    means for collecting a patient parameter disposed external to the patient, remote from the means for receiving and in communication with the means for receiving.

6. The system of claim 5, wherein the means for collecting include a sensor for sensing the patient parameter.

7. The system of claim 5, wherein the means for collecting include an interface device in electronic communication with the one or more implantable sensors for providing data from the one or more implantable sensors to the means for receiving as at least a portion of the received data.

8. The system of claim 5, wherein the means for collecting include a communication interface that provides information to patient enrolled in the clinical study.

9. The system of claim 8, wherein the communication interface provides remote, two-way communication between the patient and a caregiver.

10. The system of claim 1, wherein the one or more implantable sensors include a subcutaneously implanted sensor.

11. The system of claim 10, wherein the subcutaneously implanted sensor includes a loop recorder.

12. The system of claim 10, wherein the subcutaneously implantable sensor provides EKG data.

13. The system of claim 12, wherein the subcutaneously implantable sensor further includes means for defibrillation.

14. The system of claim 1, wherein the one or more implantable sensors include an implantable medical device for providing a therapy and sensing a parameter.

15. The system of claim 14, wherein the implantable medical device includes means for cardiac pacing.

16. The system of claim 14, wherein the implantable medical device includes means for cardiac defibrillation.

17. The system of claim 1, wherein the one or more implantable sensors is selected from the group consisting of: Temperature Sensor, Heart Rate Sensor, Cardiac Output Sensor, Cardiac Rhythm Sensor, Stroke Volume Sensor, Ejection Fraction Sensor, Pressure Sensor, Implantable External Pressure Reference Sensor, Lung Wetness/Edema Sensor, Oxygen/Oxygen Saturation Sensor, Carbon Dioxide/Carbon Dioxide Saturation Sensor, Respiration Sensor, Transthoracic Impedance Sensor, Minute Ventilation Sensor, C Reactive Protein Sensor, Protein Sensor, Elemental Sensor, pH Sensor, Lead Position Sensor, Lead Integrity Sensor, Cardiac Contractility Sensor, Vascular Dimensional Sensor, Vascular Integrity Sensor, Vascular Topographical Sensor, Cholesterol Sensor, Blood Chemistry Sensor, Salinity Sensor, Dimensional/Volume Sensor, Rhythm Motion Sensor, Cardiac Motion Sensor, Surface EKG Sensor, EGM Sensor, EEG Sensor, Neural Activity Sensor, DNA Analyzer/Sequencer, RNA Analyzer/Sequencer, Fluid Viscosity Sensor, Fluid Flow Senor, Turbulence Sensor, Alcohol Sensor, Insulin Sensor, Glucose Sensor, Lactate Sensor, Hormone Sensor, Human Chorionic Gonadotropin (hCG) Sensor (Pregnancy), Fertility Sensor, Estrogen Sensor, Testosterone Sensor, Adrenaline Sensor, Drug Sensor, Nicotine Sensor, Orientation Sensor, Motion/movement/activity Sensor, Global Location Sensor, Optical Sensor, Imaging Sensor, Acoustic Sensor, Doppler Sensor, Partial Pressure Sensor, Nitric oxide Sensor, Ultrasound Sensor, Ischemia Sensor, Spectral Analyzer, Nerve Conduction Sensor, Stroke Indicator Sensor, Seizure Sensor, Enzyme Sensor, Serotonin Sensor, Cellular State Sensor, Cancer Marker Sensor, Noradrenaline Sensor, Dopamine Sensor, Neurotransmitter Sensor, Neurotransmitter Surrogate Sensor, Hemorrhage Sensor, Ambient/Environmental Sensor, and Magnetic Sensor.

18. The system of claim 1, further comprising means for conducting post market surveillance of the drug via one of more implantable sensors.

19. The system of claim 18, wherein the implantable sensors monitor at least one parameter of a patient not enrolled in the clinical study.

20. The system of claim 1, further comprising means for providing bio-feedback information to a patient using during the post-market surveillance.

* * * * *

UNITED STATES PATENT AND TRADEMARK OFFICE
CERTIFICATE OF CORRECTION

PATENT NO. : 7,594,889 B2  Page 1 of 1
APPLICATION NO. : 11/097685
DATED : September 29, 2009
INVENTOR(S) : St. Ores et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 399 days.

Signed and Sealed this

Twenty-eighth Day of September, 2010

David J. Kappos
*Director of the United States Patent and Trademark Office*